United States Patent [19]

Palmer et al.

[11] Patent Number: 5,036,000
[45] Date of Patent: Jul. 30, 1991

[54] THRESHOLD COLOR CONTROL SYSTEM

[75] Inventors: John L. Palmer, Philadelphia; Marsha W. Timmerman, Allentown, both of Pa.

[73] Assignee: Enzymatics, Inc., Horsham, Pa.

[21] Appl. No.: 75,817

[22] Filed: Jul. 20, 1987

Related U.S. Application Data

[63] Continuation-in-part of Ser. No. 942,414, Dec. 16, 1986.

[51] Int. Cl.$^5$ .......................... C12Q 1/32; C12Q 1/54; C12M 1/40
[52] U.S. Cl. ........................................ 435/26; 435/14; 435/25; 435/174; 435/175; 435/177; 435/176; 435/182; 435/288; 436/904; 422/56
[58] Field of Search .................. 435/25, 26, 175, 176, 435/177, 178, 179, 805, 810, 10, 174, 14, 288, 182; 422/56

[56] References Cited

U.S. PATENT DOCUMENTS 3,964,871 6/1976 Hochstrasser ........................ 435/805
4,629,697 12/1986 Limbach et al. ....................... 435/26

*Primary Examiner*—Esther L. Kepplinger
*Assistant Examiner*—Toni R. Scheiner
*Attorney, Agent, or Firm*—Finnegan, Henderson, Farabow, Garrett & Dunner

[57] ABSTRACT

A system for quantitative colorimetric analysis of biological fluids or organic compounds, including NAD(P)H, or a substrate of an enzyme which reacts with the formation or consumption of NAD(P)H. Concentrations of organic substrates for example alcohol, cholesterol, uric acid, in a biological fluid such as saliva, blood or urine may be determined. The system gives a digital reading of the organic material the concentration which is sought to be determined; the concentration of NAD(P)H is determined by a color change or color "signal" when the NAD(P)H is above a threshold concentration and by the absence of a color signal when the concentration of NAD(P)H is below the threshold concentration. The system includes a chromogen, an electron-accepting reactant which, until exhausted, prevents a visible color change due to accumulation of reduced chromogen, and a catalyst. The system is capable of measuring colorimetrically without dilution concentrations of organic compounds in biological fluids which previously could not be measured in such concentration.

85 Claims, No Drawings

THRESHOLD COLOR CONTROL SYSTEM

CROSS-REFERENCE TO RELATED APPLICATIONS

This patent application in a continuation-in-part of pending patent application Ser. No. 06/942,414, filed Dec. 16, 1986 entitled "Color Control System", which is herein incorporated by reference.

BACKGROUND OF THE INVENTION

1. Field of the Invention

This invention relates to systems, more particularly a device for quantitative colorimetric analysis of organic substances concentrations generally in biological fluids. The invention also relates to a method for making such analysis. The invention also relates to a system, a device and a method which involves the reduced and oxidized coenzymes nicotinamide-adenine dinucleotide (NADH, NAD+) or nicotinamide-adenine dinucleotide phosphate (NADPH, NADP+) (collectively herein referred to as NAD(P)H and NAD(P)+) in a system, a device and a method for determination of NAD(P)H. The device may be disposable.

The invention relates to a novel and unique analog to digital colorimetric signal system, device and method which determines the concentration of NAD(P)H or of an organic substance which generates NAD(P)H in a NAD(P)+ dependent dehydrogenase reaction where the dehydrogenase is specific to the substrate.

The concentration of the NAD(P)H or of the organic substance of unknown concentration, the concentration which is determined, is ascertained by an "off"-"on" change of color, preferably quite decisive and highly distinctive, like yellow to intense blue.

The invention provides a test of extreme sensitivity and accuracy coupled with great convenience. The invention has numerous applications and uses in industrial, biomedical, medical, diagnostic (e.g., in genetic engineering) and numerous other fields as will become readily apparent to one of average skill in the art to which the invention pertains.

2. Brief Description of the Prior Art

The earlier filed patent application referred to above describes a system for colorimetrically determining the concentration of a biological molecule in an aqueous solution, such as saliva, blood, urine, or an industrial process fluid.

The contribution made by the invention disclosed by the prior application is described below. For a detailed description of the prior art, reference is made to the earlier filed pending application. Briefly, the use of dehydrogenase enzymes as specific probes for biological molecules is well known in the art. In general, a biological molecule to be assayed is oxidized by a substrate-specific dehydrogenase, and the resulting product, NAD(P)H, is either assayed directly or converted into a color signal and assayed. When NAD(P)H is assayed directly, the known fact that NAD(P)H has a substantial difference in absorbance at 340 nm than does NAD(P), is used as a measure of the amount of dehydrogenase substrate oxidized. When the NAD(P)H is converted into a color signal, an enzyme or catalyst is used to transfer the electrons from the NAD(P)H to a chromogenic molecule which accepts these electrons with a resulting change in visible color.

A serious problem that existed in all of the art prior to the earlier application is that one equivalent of dye molecule is produced for ever biological molecule that is oxidized. This limitation prevented the assay of "high" concentrations of these biological molecules, as the amount of color that would be generated by the complete or near complete oxidation of such a "high" concentration, in accordance with conventional methods, would yield colored solutions that had too high an absorbance to be read without dilution. Additionally, the "high" concentration of dye would lead to solutions wherein dye-dye interaction would cause serious deviation from the ideal as predicted by Beer's law, resulting in solutions that do not have linear relationship of absorbance versus concentration of dye. These difficulties are of more than passing concern. These "high" concentrations (too high to measure), include the normal concentration as well as the super normal concentration indicative of a disease state of most, if not all, medically important biological metabolites. Therefore, when complete or near complete oxidation of a biological molecule was used in the assay methodology common to all previous assays, a massive dilution of the medical sample was necessary to lower the concentration of the biological molecule.

The prior patent application overcomes these problems. In the invention described in that patent application less than one molecule of dye is created per molecule of NAD(P)H. This ratio of less than one to one is accomplished in a system that contains a diaphorase enzyme that catalyzes the NAD(P)H dependent reduction of a chromogen to cause a visible color change, a first substrate, which is a chromogenic electron-acceptor and a substrate for the diaphorase, which causes color to be changed when the chromogen is reduced by NAD(P)H; and a competing substrate for the diaphorase which is an electron-acceptor but which does not undergo a colorimetric change in the same region of the visible spectrum as does the chromogenic substrate. The patent application discloses methods for selecting and identifying competing substrates, all such competing substrates being substrates for the diaphorase enzyme.

Of particular note in that invention was the discovery of a class of competing substrates which prevented the generation of color unless a predetermined amount—the threshold amount—of the substance to be measured was present. This embodiment of the invention enables one skilled in the art to produce a unique, colorimetric, analog to digital converter. When the concentration of NAD(P)H is less than the threshold concentration, no color is produced. At any concentration of NAD(P)H greater than the threshold concentration, a dark color is produced. This threshold can be set at any given concentration, or a multitude of regions on a measuring device can have different concentrations, each of which will measure a different concentration as a digital "on/off" signal.

OBJECTS OF THE INVENTION

There are numerous objects of the invention. One object is to provide an accurate, precise, fast and reliable device which permits quantitative analysis of selected organic molecules normally present in organic liquids or fluids.

Another object is to provide a digital color signal giving an "off"-"on" signal for sought concentration of the unknown.

Another object is to provide an analog to digital chemical color signal device.

Another object is to provide disposable kit which will give a distinctive color at a threshold concentration of the organic molecule concentration which is to be determined.

Other objects will become apparent to one of average skill in the art in the further description of the invention.

Another object is to provide a system, a method and a device which has numerous practical applications and will contribute to the advancement of technology in the field to which the invention applies.

Another object of the invention is to provide a system, a method and a device for determination of NAD(P)H, which may be generated in situ in the presence of appropriate reactants.

Another object of the invention is to provide a system, a method and a device for determination of an organic molecule which will ultimately generate NAD(P)H in the presence of the appropriate reactants.

SUMMARY OF AND FURTHER BACKGROUND OF THE INVENTION

In conjunction with ongoing research work, it was accidentally discovered that the diaphorase is not any longer a required component of the system—and method—described in the earlier patent application.

An experiment was carried out in which an aqueous buffer contaminated with alcohol was mixed with the enzymes alcohol dehydrogenase and diaphorase, the coenzyme and electron-carrier NAD, and the chromogen MTT. This reaction rapidly turned to a dark blue color due to the presence of alcohol contamination. Then the competing substrate, ferricyanide, was added to the reaction mixture. Surprisingly, the reaction lost its dark blue color, and returned to the color it was without ethanol contamination. When a concentration of ethanol greater than one half the concentration of ferricyanide was added, the reaction again turned blue. What occurred apparently in this experiment, is that the alcohol dehydrogenase oxidized the contaminant alcohol in the presence of NAD to produce an oxidized product, acetaldehyde, and a reduced coenzyme, NADH. The diaphorase then used the NADH to reduce the chromogenic substrate MTT to form a formazan dye and regenerate NAD. It was found that no NADH will be generated by diaphorase in the presence of formazan dye and NAD; thus it was concluded that the reaction was irreversible. It was further shown that no loss of color occurs when excess NAD is added to solution containing formazan dye and diaphorase. Therefore, it was concluded that the ferricyanide was capable of directly oxidizing the formazan dye to regenerate the uncolored chromogenic substrate.

This direct effect of ferricyanide was not foreseen in conjunction with the work disclosed in the earlier patent application. It was proposed in that application that the competing substrate worked exclusively due to it being a substrate for the enzyme diaphorase that had preferred access to the diaphorase active site. The present invention is that much more unexpected in that benzoquinone and ferricyanide behave identically in a reaction containing diaphorase. However, in the absence of diaphorase only the ferricyanide (as compared to the benzoquinone) causes the decrease in color.

This unexpected experimental observation brought about two principal embodiments of this invention, whereby it was possible to reduce the color generated upon the NAD(P)H dependent reduction of a chromogenic molecule to within a readable range.

In a first embodiment of the invention the competing substrate (used in the work disclosed in the earlier patent application) is omitted. In the system of the invention, there is used a reactant that is not a substrate for the diaphorase, but which does react with and render colorless the dye formed upon NAD(P)H dependent reduction of the chromogen. In this embodiment, no color is generated as long as the reactant is present. The reactant reacts with the dye formed from the chromogen reduction and eliminates or prevents the formation of color upon the formation by oxidation of the chromogen. When the reactant is substantially exhausted, its ability to react with the dye is similarly exhausted, and dye that is formed gives a color signal.

In accordance with this embodiment, the system of the invention comprises NAD(P)H (or a source for NAD(P)H to generate NAD(P)H in situ), a chromogen which upon catalytic reduction generates a dye (as NAD(P)H is oxidized to NAD(P)) and a reactant for the dye which is capable of—and does—oxidize the dye as it is formed to form again a chromogen, thus preventing the formation of color prematurely. The catalyst may be diaphorase or a non-protein catalyst as further disclosed hereinafter.

The second embodiment of the invention also takes advantage of the newly discovered observation that the catalyst does not have to transfer the NAD(P)H derived electrons directly to the reactant.

It was found in accordance with the invention, that in the system—and the method—the diaphorase can be omitted. Instead, a non-protein catalyst is used. This is greatly advantageous, as the cost of diaphorase can be appreciable in total product material cost, and the diaphorase is more susceptible to certain temperature, pH (and other conditions which are not optimum for that enzyme) than a catalyst that is an organic or inorganic molecule (but not enzymatic like diaphorase).

In accordance with this embodiment of the invention, there is used an electron-carrier catalyst which oxidizes NAD(P)H and transfers electrons to the chromogen forming a formazan in the presence of the reactant. The catalyst, as explained further below is an organic or inorganic molecule other than diaphorase.

Such electron-carrier catalysts are known in the art. However, in the methods of the prior art (for instance, U.S. Pat. Nos. 4,024,021; 4,351,899 and others) one molecule of dye is produced per molecule of NAD(P)H. In the present system, as described further below, there is produced less than 1 molecule of reduced chromogen per 1 equivalent of NAD(P)H present or produced in the system of the invention.

DETAILED DISCUSSION OF THE INVENTION

The colorimetric assay system of the invention comprises a prodye or chromogen which is an electron-acceptor for NAD(P)H and which is capable of changing color in the visible range. A typical chromogen is a tetrazolium salt. In the system of the invention, the chromogen may be colorless to start with and develop a color upon reduction or the compound may be colored to start with and become colorless as the reaction is completed, or the chromogen may be a light color and change to a deep or other distinctive color, like from yellow to deep blue or purple.

The system of the invention also includes NAD(P)H which may be generated in situ as described hereafter, and a reactant (or reductant) which is capable of accepting electrons from reduced chromogen and/or from NAD(P)H and an electron-carrier catalyst which is capable of transferring electrons from NAD(P)H to the chromogen and at least theoretically, vice-versa.

The reactant used in the invention is capable of preventing the accumulation of reduced chromogen and thus the development of color attributable to the reduced chromogen. Thus, if the chromogen is a light yellow, for instance and the reduced chromogen deep blue, the reactant reacts with the reduced chromogen as it is formed, causing it to revert virtually instantaneously to or essentially causing it to remain in its chromogen state (yellow) and not to develop the deep blue color. Thus, the reactant, in accordance with the invention is capable of regenerating the chromogen. These conditions prevail until the reactant is exhausted.

Thereafter, and in the presence of NAD(P)H, the full color of the reduced chromogen will develop virtually instantaneously, in this illustration, the deep blue color. Because of the nature of the reaction, the presence of essentially a trace amount of chromogen will generate the color, for practical purposes approximately 1 mM. The concentration of reactant with respect to the chromogen is not critical and may for instance be 50, 100, 200, 300 mM, or more. When there still is NAD(P)H present and the reactant is depleted, i.e., an excess of NAD(P)H is present in the system over the amount of electron-accepting ability of reactant, color will instantaneously develop. For purposes of definition, this is the "threshold" amount of NAD(P)H. Thus the system gives a digital reading of two states, and two states only: an "off" and "on" state, the first corresponding to no "color", the second to "color". By "on" and "off", there is meant as described above a "change of color" not only "color" to "colorless" or vice-versa. Thus, unlike an embodiment of the earlier referred to patent application (and unlike many conventional prior art methods and systems), in the present invention the concentration of the NAD(P)H does not correspond to an intensity of color generated, nor it is necessary to perform any plotting (color generated vs. standard color curve) to know the concentration of the NAD(P)H or of the organic compound (or substrate) which generated the NAD(P)H, when such substrate is present.

In accordance with the teaching of the present invention, it will be seen that in cases where the color is in an "on" state there may be and there is generally likely to be present an excess of NAD(P)H in excess of the trace, or as stated above about 1 mM chromogen necessary to develop the color upon depletion of the reactant. As an illustration, in a system which at starting conditions contains 20 mM of reactant, 1 mM of chromogen and 40 mM of NAD(P)H there results (in the situation where 1 mole of reactant accepts 2 electrons from 1 mole of NAD(P)H), 20 mM of depleted reactant, 1 mM of reduced chromogen and 19 mM of excess NAD(P)H. This excess of NAD(P)H does not convey relevant information for the purpose of the invention.

The system will have given an "on" reading at the instant when and by the development of strong color when a trace or in this instance approximately 1 mM of reduced chromogen will have been formed by reaction with the 1 mM of NAD(P)H.

Also in accordance with the invention, it will be appreciated that the invention is not limited to absolute numbers, as illustrated above for instance for the 1 mM. What is more significant is the color formation attributable to the reduced chromogen or dye. Ideally the extinction coefficient of the reduced chromogen is so high that less than 1 mM of reduced chromogen is required to cause an abrupt and strong positive color development or signal. The extinction coefficient of reduced chromogens are known and when not known or readily available, can be readily determined by one of average skill in the art without undue experimentation. Ideally, therefore, a chromogen is to be selected which in the reduced state gives a "clear", sharp, unequivocal, distinct color change in the system of the invention upon reaction of the NAD(P)H.

In the situation where reactant is not depleted when NAD(P)H is depleted, it is evident that chromogen will still be present but no excess reduced chromogen be formed and hence no color change occurs.

There is an important aspect of the invention which will become more apparent from the discussion which follows.

In accordance with the invention, it has been discovered that the concentration of NAD(P)H can be measured very accurately and efficiently in an "on-off" digital manner. Where the reactant is reduced until essentially depleted, a visible color develops if and only if excess NAD(P)H is present; if none is present, no color develops. Thus, in accordance with the invention, a particular pre-selected concentration of reactant corresponds to a threshold accumulation of NAD(P)H. If it is above the threshold, a color will develop when the reactant is exhausted, but no color, when the reactant is not exhausted and the NAD(P)H is below the threshold. In accordance with the invention, several concentrations of the reactant are pre-selected and the development of color corresponds to concentration of the NAD(P)H in the system to be determined, whether it is a liquid or preferably, a device with a solid support for the reactants.

The determined concentration of NAD(P)H also corresponds to the concentration of the organic compound which is sought to be determined, if one is present and which generates NAD(P)H (in the presence of the appropriate dehydrogenase).

At the threshold, the concentration of reactant is equal to 1 or 2 times that of NAD(P)H, this being dependent on whether the reactant is capable of accepting 2 or 1 electrons from the NAD(P)H. Where the reactant is capable of accepting 2 electrons, the relationship is 1 to 1, and it is 2 to 1 when the reactant is capable of accepting 1 electron from the NAD(P)H.

In addition to the system of the invention, and various devices, the invention provides a method for measuring NAD(P)H which may be generated in situ by an organic substrate the concentration of which is sought to be determined. In that embodiment, an appropriate dehydrogenase specific for the substrate is also present, as will be described further hereinafter.

The process of the invention comprises bringing together the necessary components of the system. The components or reactants are conveniently in an appropriate medium such as a liquid (e.g., aqueous) medium generally for most practical embodiments in or on an appropriate physical support. Such physical supports are known in the literature and are described in the parent patent application referenced herein above.

There are a wide variety of suitable physical supports that can be used in this invention. In general, the support member may be any material capable of bearing the system for exposure to the liquid solution to be measured, preferably the support is inert enough to the reactants (and products) not to interfere adversely with the reaction. Specific examples of support materials are sheets, rods, webs, filters, strips and similar forms of glass, cellulose, wood, metal, or polymerics such as polyethylene, polypropylene, polyalkyleneacetate, polycarbonates, and the like, or textiles and the like. In one embodiment of the invention, the system can be incorporated into a bibulous material that is capable of taking up, by hydration or capillary action or other similar means, a set and reproducible amount of liquid. Materials that meet these criteria can be manufactured from a wide variety of solids. Examples of solid supports are: metal oxide, as typified by Norton Corporation's (Worcester, MA) controlled pore alumina HSA catalytic rings; polymeric materials, as typified by Nucleopore controlled-pore polycarbonate membranes; and hybrid ceramic/polymer materials as typified by Amerace's polyvinyl-chloride sheets that contain embedded silica particles. Such hybrid sheets are described in U.S. Pat. No. 4,169,014, which describes the coupling of active enzymes to these sheets. This patent does not address the utility of these sheets containing said active enzymes in containing a known and calibrated volume of liquid material.

In another ideal embodiment of the invention, the ingredients of the system may be incorporated into a multilayer dry gel which is situated inside a controlled volume capillary. When aqueous sample is introduced into the capillary, the gel, which may be made of any organic or synthetic polymer, like: gelatin, agarose, agar, polyvinyl alcohol, polyvinyl pyrolidone, alginate, carrageenan, dextran, xanthan gum, or mixtures of the above, swells and rehydrates, activating the dried system ingredients. A non-obvious advantage of this system is that various ingredients of the system, for example the reactant and various buffer salts needed to stabilize a dehydrogenase enzyme, do not have to see one another (or be in contact with each other) during long term storage. Thus, storage incompatibilities of system ingredients is not encountered in multilayer systems.

The invention is not limited to the particular physical embodiments described above. There are numerous appropriate physical arrangements that are described in the literature and others can be built by one of average skill in the art.

In accordance with the invention, the ingredients of the system are brought together as a reaction mixture which contains the chromogen, the electron-accepting reactant and the catalyst. To the mixture there is added NAD(P)H until a color change occurs. The color change is indicative of the exhaustion of the reactant and that chromogen has been reduced to a strong visible color.

In accordance with the method, various linearly related concentrations of the reactant can be provided in different regions of an assay device. For example, linearly related differing reactant concentrations can be situated along the "X" axis of a device containing this system. Thus, an "on" signal will be generated at a different linearly related concentration of NAD(P)H or substance that generates NAD(P)H along this "X" axis. When the reactant is situated in this manner, increasing either linearly along the "X" axis or in steps of increasing or decreasing concentration, the amount of NAD(P)H that is introduced into the system to effect measurement, will be determined by visual inspection of the distance that "on" signal, that is to say, color change, is propagated along the "X" axis.

This embodiment provides a practical measuring device of numerous industrial and commercial applications.

When in accordance with the invention it is desired to measure the concentration of an organic substrate, the method comprises bringing together the chromogen, the electron-accepting reactant, the catalyst, NAD(P)+ and a suitable specific dehydrogenase for the organic substrate to be measured. To this reaction mixture there is added in increasing amounts of the substrate to be measured, causing the substrate to be oxidized, the NAD(P)+ to be reduced to yield NAD(P)H and the reaction to proceed until color is generated, as described above. At that point the reactant is depleted and NAD(P)H generated from the substrate reacts with chromogen to yield reduced chromogen and a highly visible color change indicative of the concentration of the substrate.

Generally the reaction is carried out in a buffered environment at a pH preferably optimum for the catalyst and enzyme used, as is described hereinafter and at optimum temperature.

The reaction may be carried out in a liquid or on a suitable physical carrier which allows for the reactants to react as described.

Although the invention is not limited by any particular scientific theory or principle, the invention can be considered as having two principal embodiments.

In the first embodiment, the reactant reacts with the reduced chromogen as it is produced by the catalytic reduction of the chromogen and thus prevents the formation of colored chromogen. When the reactant is all consumed as discussed above, colored (reduced) chromogen is then generated catalytically, where color is indicative of the presence of the organic molecule, the concentration of which is sought to be determined.

In the second embodiment, it appears that the reactant will accept electrons directly from, and thus react directly and preferentially with, the NAD(P)H in the system, or as it is formed from the organic molecule. When it is exhausted, the NAD(P)H will react with the chromogen forming reduced chromogen, as described above.

It is not essential that a distinction between the two embodiments be made in the practice of the invention since in both cases color produced by the reduced chromogen readable (without dilution) in the visible range will be formed.

It will have become apparent from the discussion of the invention that where the threshold is reached—and an "on" signal is read—there is produced less than 1 equivalent of dye (reduced chromogen) per equivalent of NAD(P)H at any concentration of NAD(P)H, this being another distinction over the prior art.

Reactants which are useful for use in the invention are generally weak organic and inorganic oxidizing agents which are stable in aqueous environment at the operative temperature and pH. A great variety of reactants are available for use in the invention. A screening test has been developed which allows the determination of suitable candidate reactants without undue experimentation.

For the test an equivalent of NAD(P)H is added to an equivalent of chromogen and a catalytic amount of diaphorase in a flask, and the resulting dye is aliquoted into test tubes. A candidate reactant is added to the test tubes. A reactant passes the test if the dye color is removed, i.e. the reduced chromogen has been reverted to chromogen. For best results it is also necessary that the reactant be incapable of inactivating the diaphorase or be inert with respect to another catalyst used. For this purpose, the following test is used. A known amount of reactant, for example 10 mM, is mixed with about 1 mM chromogen, and a catalytic amount of diaphorase. Aliquots of NAD(P)H are added to this reaction medium, 2 mM at a time. The reactant is said to pass the test if the solution containing 4 mM NAD(P)H is colorless, while the solution containing 12 mM demonstrated the presence of reduced chromogen or dye. This second stage test also will determine if the reactant has a 1 to 1 or a 2 to 1 reactivity with the dye.

The second test discussed above also identifies a reactant that will not accept electrons from the reduced chromogen, but instead acted by preferentially receiving electrons from the NAD(P)H. In general, any similar test that tests for the absence of color change when reactant is substantially present can be used for the tests described as will be obvious to anyone with average skill in the art.

In accordance with the invention, by weak oxidizing agents for use in the invention, there is meant any compound or element that is stable for which is more electron accepting than is NAD(P)H/NAD(P), as measured by standard electronegativity assays, for example, as discussed in the well known textbook "Physical Chemistry" by Walter J. Moore, published by Prentice-Hall, New Jersey (1972), incorporated herein by reference. Preferably the compound should be stable for about an hour in aqueous solution. Examples of molecules that are more electron-accepting than the NAD(P)H/NAD(P) couple are organo-metal salts, for example: ferric salts, e.g. the triethyloiamine chloride salt of Fe(III), the Fe(III) citrate complex, the Fe(III) EDTA complex, and the Fe(III) sorbitol complex; cobalt, for example the Co (III) compounds hexamino cobalt (III) chloride, potassium hexacyanocobaltate (III), and sodium hexanitrocobaltate (III), and the like; and similar salts of other, electronegative transition metal ions. A reactant of choice is ferricyanide, and its alkali metal salts like sodium, potassium, and other equivalent water-soluble iron salts, or other equivalent.

The choice of reactant is not limited to metals, but rather to the requirement that it be an electron-accepting molecule that is stable in aqueous solution.

Thus, inorganic oxidizing agents like sodium or potassium periodate have been utilized as reactant molecules, as have organic oxidizing agents, for example dithiols, like aromatic (benzyl)-nitro-substituted thiols, typified by para-nitrobenzyldisulfide, 2,2'-dithiobis-(pyridine-N-oxide), and 2,2'-dithiobis(4-tert-butyl-1-isopropylimidazole). Various organic peroxides are suitable inclusive of hydrogen peroxide, other organic peroxides, for example the peracids of lower alkyl peracids, like acetic, formic and the like, and molecules of the general structure R-O-O-R' wherein R and R' are or are not equal and are members of the general class of aliphatic (e.g. lower alkyl), or aromatic, or cyclic hydrocarbons, or are members of the above classes containing substitutions of nitrogen, oxygen, thio, cyano, halide (like bromo- or chloro-) or the like.

It should be especially noted that heterocyclic organic compounds can be utilized as the reactant, like substituted triazones, for example melamine, and the halo substituted melamines like trichloromelamine, and also halo substituted and unsubstituted electron-accepting dyes, for example N-trifluoromethylflavin.

Suitable chromogens for use in the invention are abundant. Conveniently they are tetrazolium salts. Illustrations are 2-(2'-triazolyl)-3,5-diphenyl tetrazolium bromide (MTT), 3,3' dimethoxy-4,4'-diphenylene)bis[2-(p-nitrophenyl)-5-phenyltetrazoliumchloride] (NTB), 2-(p-nitrophenyl)-3-(p-iodophenyl)-5-phenyltetrazolium-chloride (INT) or 2-(4,5-dimethyl-2'-thiazolyl)-3,5-diphenyltetrazolium-bomide (4,5-MTT). The concentration of the tetrazolium salt is rather limited by the solubilities of tetrazolium salts and the ultimately formed formazan and generally is less than 10 mM, with the lower limit set by the amount of reduced chromogen necessary to give a clear and distinct color signal, generally greater than 0.05 mM. Again, it should be noted, the invention is not limited to particular absolute values.

Other tetrazolium salts are disclosed in U.S. Pat. Nos. 4,490,465, column 6; 4,491,631, column 14; 4,598,042, column 18; 4,351,899, column 2; 4,271,265, column 5; 4,247,633, column 3; 4,223,090, column 3; 4,215,917, column 3; 4,142,938, column 3; 4,024,021, column 3; 3,867,259, column 2; 3,867,258, column 5; 3,791,931, column 1; 4,254,222, column 5, incorporated herein by reference.

To maintain the pH of the solution at a desired value during the reaction, a conventional buffer solution is used. Examples of the buffer solution are found in U.S. Pat. Nos. 4,416,983, column 3; 4,592,996, column 5; 4,271,265, column 5; 3,867,259, column 4; 3,867,258, column 2; 4,254,722, column 3; incorporated herein by reference.

In the case where the NAD(P)H is generated by the action of a specific dehydrogenase acting on its specific substrate, it may be advantageous to incorporate into the buffers molecules that will react with and trap, immobilize, etc., the oxidized specific substrate. These compounds are generally amine containing compounds, for example tris, or glycine that can also be utilized for pH control. Compounds that are especially useful for this trapping function are those of the general class known as alpha-effect amines. Alpha-effect amines are those amine containing compounds that contain an atom that has unpaired electrons adjacent to the amine functional group. Examples of alpha-effect amines that can be advantageously incorporated into this system are hydrazine, N-substituted hydrazines, hydroxylamine, and O-substituted hydroxylamines, especially those O-substituted hydroxylamines that are stable to drying due to their high boiling nature and low vapor pressure. An especially suited compound of this class is carboxymethoxyamine.

Electron-carriers or transfer catalysts suitable for the invention are substances which have oxidizing activity on NAD(P)H to NAD(P)+ and no detrimental action on the coenzyme cyclic reaction. Such catalysts include, other than diaphorase, polycyclic (generally aromatic) unsaturated dyes of various subclasses. Illustrative are benzoquinones, especially with aromatic substitution like phenyl and other aromatic compounds like benzoquinhydrone (quinhydrone). Other aromatic compounds which in the presence of a chromogen will react preferentially with NAD(P)H are suitable including those having single or multiple aromatic rings (fused or not) which may have various substituents. These compounds may generate a color when reduced into the presence of NAD(P)H. Specific typical useful color-generating electron-carriers include phenazonium methosulfate (PMS), N-methyl-PMS, meldola blue, pyrocyanine, N-methylphenazonium methosulfate, methylene blue, riboflavin alloxazine, 9 amino-1,2,3,4-tetrahydroacridine, substituted anthraquinones (saturated or unsaturated) which are color-generating are various amino-, alkyl- (especially lower alkyl, like methyl), halo- (like chloro-, or bromo-), hydroxy-, nitro-, sulfonic acid, alkoxy(like methoxy) anthraquinones. Such anthraquinones are listed in the Handbook of Chemistry and Physics, 62nd Ed (1981-1982) (Section C) and are known under such common names as purpurin, flavopurpurine, hydroxy-chrysazin, anthraragallol, quinalirarin, tufiopin, hystazin, aloemedin, alizarin; other aromatic color-generating compounds like azulene, benzaurin, and other equivalent compounds having the same function and effect. When the selected catalyst generates color, the color should not be generated in the same visible spectrum where the color of the chromogen upon reduction will be generated.

Generally the embodiment of the invention involving diaphorase is more efficient; however, where conditions of the system are such that they might tend to adversely affect the stability of the enzyme, the non-protein electron-carrier catalysts are preferred. Benzoquinone is not a desired catalyst electron-transfer compound for the invention.

In accordance with the invention, it is advantageous to provide the catalytic electron-transfer in the presence of a salt, which may be preferably an inorganic salt. Palladium salt is used to increase the catalytic ability of meldola blue. Other salts have equivalent usefulness. Of particular interest are organic ligants of metals like ferrocene (dicyclopentadienyl iron). The noble metals like platinum, palladium in catalytic amounts enhance the catalytic activity of the catalyst. Suitable are water-soluble salts of palladium like palladium chloride.

Virtually the concentration of any organic compound which is a substrate for a NAD(P)-linked dehydrogenase system can be determined in accordance with the invention. Organic compounds of interest include sugars, carbohydrates, e.g. glucose; galactose; ketones; organic acids like lactic acid, uric acid; alcohols like methanol, ethanol, idiotol, sorbitol, inositol; aldehydes like formaldehyde, acetaldehyde; proteins, albumen bilirubin, beta-hydroxybutyrate; nitrates; antigens (like hepatitis B surface antigen, antigen(s) of acquired immune deficiency syndrome, immuno deficiency virus, and others), amino acids or nucleotide sequences; cholesterol, triglycerides, glycerol-3-phosphate; glycine lactate, and various other organic substrates that are reactive to enzyme-catalyzed dehydrogenation or hydrogenation and others disclosed in the literature.

Commonly the substrate is present in a biological fluid like serum, blood, urine, semen, saliva, cerebrospinal fluid or other liquids of humans or other mammals for instance of other species.

When the substrate is present for the determination of its concentration, the system also includes a specific dehydrogenase for the specific substrate. Dehydrogenases are of course known. Typical dehydrogenase are the following commercially available dehydrogenases or to be available dehydrogenases or any other dehydrogenase can be substituted for the dehydrogenase used in each specific example: glucose dehydrogenase, L-glutamic dehydrogenase, glyoxylate reductase, hydroxybutyrate dehydrogenase, polyol dehydrogenase, sorbitol dehydrogenase, myo-inositol dehydrogenase, isocitrate dehydrogenase, 2-ketoglutarate dehydrogenase, leucine dehydrogenase, lipoamide dehydrogenase, malic dehydrogenase, malic enzyme, succinate semialdehyde oxidoreductase, 5-10-methylenetetrahydrofolate dehydrogenase, NADH peroxidase, cytochrome C reductase, octopine dehydrogenase, 3-phosphoglycerate dehydrogenase, dihydropteridine reductase, pyruvate dehydrogenase, sacharopine dehydrogenase, uridine-5'-diphosphate dehydrogenase, xylulose reductase, 6-phosphogluconic dehydrogenase, alanine dehydrogenase, dihydrofolate reductase, glucose-6-phosphate dehydrogenase, hydroxyacyl CoA dehydrogenase, 1 acetate dehydrogenase, glycerophosphate dehydrogenase, glycerol dehydrogenase, glyceraldehyde-3-phosphate dehydrogenase, alcohol dehydrogenase, aldehyde dehydrogenase, alpha-hydroxysteroid dehydrogenase, beta-hydroxysteroid dehydrogenase, ferredoxin oxido reductase, formaldehyde dehydrogenase, formate dehydrogenase, fructose dehydrogenase, and galactose dehydrogenase and other dehydrogenases which fulfill the equivalent function.

It is important to note that in accordance with the invention, the compound, the concentration which is sought to be determined, need not be itself a substrate for the dehydrogenase. It is sufficient that it be capable of, and generate, a substrate for the dehydrogenase, for instance a triglyceride.

The device of the invention, which is often discardable after the threshold color will (or will not) have developed comprises a support member bearing a single or a plurality of concentrations of the reactant. The support member is not critical in the sense that a specific material of construction is required although several forms of the preferred embodiment will be described hereinafter. In general, the support member may be of any material capable of bearing the reactant and the other components of the system, if necessary, for exposure to the solution to be tested. Specific examples of support members are webs, sticks, strips, splinters, sheets, rods and like forms of glass, metal, wood, paper; polymerics such as polythylene, polypropylene, polyalkylene acetate, polycarbonates and the like; gelatin and like materials; textiles and the like. Preferred materials are the bibulous materials which may be impregnated with solutions of reactant compositions, such as filter papers, blotting papers and like bibulous materials. Physical systems of the invention have been described above.

The reactant components of the assay system of the invention are preferably prepared in a liquid form for deposit upon the support member. Once placed on the support member, the reactant compositions in solution are dried to adhere the compositions to the support member. Generally, adhesion of the reactant compositions to the support member is conveniently effected when the support member is a bibulous material. Conventionally employed inert filters, binders, surfactants and the like may be incorporated into the reagent compositions when desired. Certain binders such as resin gums are advantageously incorporated into the reactant compositions to assist in adhering them to non-porous support members such as metal, glass or non-porous polymeric materials. For product elegance and accuracy, it is desirable that the color change in each indicator zone of the devices of the invention be clear, sharp, unequivocal and strongly positive.

The device may be used as disclosed in U.S. Pat. No. 4,059,407 by immersion in the biological solution to be tested as for instance in a capillary. When it is desired that the device function in a thermometer-like fashion, the device is adapted to have several sites or regions. The device may be constructed as disclosed in said U.S. Pat. No.4,059,407. Reference is also made to its Figures which illustrate suitable physical embodiments of the present invention.

The following examples are merely illustrative of the invention and of the best mode now contemplated by the inventors presently. The examples are not to be construed as limiting the invention. One skilled in the art without undue experimentation can make various substitutions and variations and by equivalent means, performing in substantially the same manner, obtain substantially the same results without departing from the teaching and spirit of the invention.

All parts are by weight unless indicated otherwise.

Example 1

A reaction mixture containing:
  100 mM Tris buffer pH 9
  21 mM NAD
  1 mM MTT chromogen
  1.25 mM meldola blue
  0.1 mM palladium (II) chloride
  100 IU/ml alcohol dehydrogenase
  40 mM potassium ferricyanide
is treated with various concentrations of alcohol. It is found that this reaction is light grey when 18 mM alcohol is added, and dark blue when 22 mM alcohol is added.

Example 2

To a reaction containing:
  200 mM phosphate buffer pH 7.6
  1 mM MTT
  1.5 mM PMS
  0.1 mM ferrocene
  10 mM dimethylperoxide
is added various concentrations of NAD(P)H. It is found that the reaction remains essentially colorless when up to about 10 mM of NAD(P)H is added. When concentrations of NAD(P)H greater than 10 mM are added, the reaction turns bright blue.

Example 3

To a reaction containing:
  mM Tris buffer pH 7.3
  1 mM MTT
  1 mM PMSA
  6 mM NAD
  12 mM ferricyanide
  100 IU/ml lactic dehydrogenase
is added various concentration of lactic acid pH 7 solution. It is found that the reactions remain faint yellow when less than 6 mM of lactic acid is added, but turns bright blue when concentrations of lactic acid greater than this threshold are added.

Example 4

An absorbent paper is soaked with a reaction containing:
  300 mM Tris-chloride pH 9.0
  21 mM NAD
  40 mM potassium ferricyanide
  1 mM PMS
  1 mM MTT
  100 IU/ml alcohol dehydrogenase
and the paper is dried and cut into 0.5 inch diameter circles. 20 ul of solution containing various concentration of alcohol are added to each circle. It is found that circles exposed to 15 and 18 mM alcohol remain pale yellow, while circles exposed to 20 and 22 mM alcohol turn bright blue.

As discussed above, the invention can also be used to determine the concentration of molecules that are not themselves substrates for a dehydrogenase, as long as they can be acted upon to become dehydrogenase substrates. The following examples demonstrate this embodiment. In the case where triglyceride levels are measured after by conversion to glycerol, which is then oxidized by glycerol dehydrogenase to form NAD(P)H.

Example 5

For the determination of triglyceride in an aqueous sample, for example serum, place down a 1-4 mil thick (wet) layer of 5-35% gelatin containing:
  10-800 IU/ml glycerol dehydrogenase
  50-1600 mM Tris base pH 9.0
  10 mM NAD
  0.02% triton X-704
  0.1% palladium (II) chloride
  1 mM PMS This layer is overlaid with a separating layer that contains only gelatin or gelatin and other gelling agents and/or detergents. Another laid is layed down on top of the above that contains various linearly related step gradient concentrations. For example from 0 to 45 mM of either potassium or sodium ferricyanide or Fe(III)-/EDTA reactant plus approximately 0.75 mM of chromogen, e.g. MTT. The above sandwich is overlaid with another separating layer as discussed above, then finally the entire stack is overlaid with a spreading layer that will cleanly wick the aqueous sample over the entire measuring area, such as:
  5% microcrystalline cellulose
  2.5% gelatin
  0.03% Triton X-100
  200 IU/ml lipase
  50 IU/ml protease, for example alpha-chymotrypsin.

The entire multilayer gel is dried in hot (37° C.), dry air. The dry gel package is placed inside a capillary which will contain a set and reproducible volume of liquid sample per unit area of measuring surface.

Upon introduction of an aqueous sample of triglyceride, the lipase and protease hydrolyze the triglyceride to produce free glycerol. The free glycerol diffuses in the hydrated gel to the glycerol dehydrogenase whereon it is oxidized to produce NAD(P)H, which reacts with the reactant or the chromogen, as the case may be, to indicate the concentration of triglyceride in the sample.

As an alternative to the above, glycerol dehydrogenase may be substituted for by the combination of ATP, glycerol kinase, and glycerol phosphate dehydrogenase, or other suitable combinations as will be readily apparent to those with average skill in the art.

As disclosed in the parent case, this invention can also be used with any mixture of enzymes to assay a biological molecule providing one of the resulting products of this mixture or string of enzyme is NAD(H) or NAD(P)H.

The system of the invention as noted above will normally contain as is known, various buffers compatible with the enzymes, stabilizers (for the enzymes on the resulting dyes) and, if desired, wetting agents. Illustrations are BSA, polyalcohols, mild reducing agents and non-ionic wetting agents. The pH is generally in the range of about 4 to about 11 (being optimized for the different enzymes used). The optimum pH ranges for different enzymes, or some enzymes of different origins are known. For instance, amongst the dehydrogenases, alcohol dehydrogenase has an optimum pH of 9.0, and lactic acid dehydrogenase has an optimum pH of 8.0. Amongst the diaphorases that from pig's heart has an optimum pH of 6.0, that from microorganisms, a pH of 7.3. Thus one skilled in the art will find it advisable to adjust the environment wherein the enzymes are to be active (be it the filter paper strip, the test tube, or other liquid or solid medium, etc.) at the optimum pH or within or close to the optimum range or value. It should be noted, that in the case of the multilayer device discussed above, all layers do not have to be stored (or do not have) at the same pH, which is greatly advantageous in storage shelf life of the ingredients.

Also useful in the practice of the invention will be chemicals that form gels or films that permit storing the essential ingredients in a dry state and rehydrating in the presence of an aqueous solution and controlling color generation.

For such known chemicals see U.S. Pat. No. 4,556,634, column 4, which passage is incorporated herein by reference.

For the purpose of this invention, the "threshold" is defined to mean as color change state which is indicative of the concentration of NAD(P)H: when the concentration of NAD(P)H is less than a threshold, no color exists; when the concentration of NAD(P)H is above the threshold, the clear, sharp, unequivocal preferably strong color will be produced. Where the reduced chromogen is colorless, the reverse situation applies.

Prior art provides description of devices, often disposable which may be used in the practice of this invention as such or in a modification of such devices. The reagents and the reactions (and their sequence) of the system of the invention is novel and unobvious. Reference for such devices is made to U.S. Pat. Nos. 4,059,407; and the patents listed therein; 3,464,871; U.S. Pat. No. 3,992,158 and the later patent referring to this patent describes a device that is particularly useful to this invention. These patents describe a multilayer analytical element that will change color in the presence of an analyzed molecule. The technology discussed in these patents yields an analog color signal for an analog concentration in-put. The device and analytical element described can be modified in light of and with knowledge of the present invention to create a digital color signal. U.S. Pat. Nos. 3,485,587 and 3,164,534 also describe a device that could be modified with the invented technology to improve them to register a digital "on-/off" type signal.

Patents which also have been considered in the preparation of this patent application (in addition to those listed in the parent application) include PCT Publication W085/01747.

It is to be noted that it is within the scope of the invention to use more than one reactant (inert with respect to each other) which will be sequentially consumed by the NAD(P)H in accordance with the invention. Likewise there may be used more than one chromogen. Similarly, the system can be used to determine more than one organic compound (with their respective enzyme systems), which compounds may have different reactivity levels with respect to the other reactants.

It is within the scope of the invention also to use the method of the invention on a continuous basis in a device adapted to feed the reactants to a multiplicity of reaction zones for the reactions to take place and the color change indications to develop.

Such device is likely to be of particular interest for industrial purposes like monitoring the absence, presence or concentration of organic compounds.

The invention has been described in detail wit particular reference to certain preferred embodiments thereof, but it will be understood that variations and modifications and their equivalents can be effected within the spirit and scope of the invention as claimed.

We claim:

1. A colorimetric assay system for measurement of the concentration of NAD(P)H, NAD(P), or an analyte in a sample, which analyte reacts to form or consume NAD(P)H, wherein the assay system comprises:

a chromogen which is capable of accepting electrons from NAD(P)H and which produces a color change upon reduction by NAD(P)H, a non-chromogenic competing reactant capable of accepting electrons from NAD(P)H, in an amount sufficient to increase the range of concentrations that can be measured by the color change of the chromogen when the non-chromogenic competing reactant is reduced, wherein the non-chromogenic competing reactant prevents a visible color change due to accumulation of reduced chromogen until a predetermined threshold amount of NAD(P)H is exceeded, and an electron carrier catalyst capable of transferring electrons from NAD(P)H to the chromogen, wherein the change in color caused by the reduction of the chromogen occurs in a ratio of less than one molecule of dye for each molecule of NAD(P)H produced and is indicative of the concentration to be determined.

2. The assay system of claim 1 wherein the non-chromogenic competing reactint is capable of accepting electrons directly from NAD(P)H, from reduced chromogen, or from both NAD(P)H and reduced chromogen.

3. The assay system of claim 1 wherein the non-chromogenic competing reactant is capable of oxidizing the reduced chromogen.

4. The assay system of claim 2 wherein the reactant accepts electrons directly from NAD(P)H and reacts preferentially with the NAD(P)H.

5. The assay system of claim 2 wherein the non-chromogenic competing reactant accepts electrons from both the reduced chromogen and the NAD(P)H.

6. The assay system of claim 1 wherein the non-chromogenic competing reactant is a weak oxidizing agent which accepts electrons more readily than NAD(P).

7. The assay system of claim 6 wherein the non-chromogenic competing reactant is selected from the group consisting of triethylenediamine chloride salt of Fe(III), Fe(III) citrate complex, Fe(III) EDTA complex, Fe(III) sorbitol complex, hexamino cobalt (III) chloride, potassium hexcacyanocobaltate (III) and sodium hexanitrocobaltate (III).

8. The assay system of claim 6 wherein the non-chromogenic competing reactant is selected from the group consisting of sodium potassium periodate, paranitrobenzyl disulfide, 2,2'-dithiobis-(pyride-N-oxide), and 2,2'-dithiobis(4-tert-butyl-1-isopropyl imidazole).

9. The assay system of claim 6 wherein the non-chromogenic competing reactant is a water soluble alkali metal salt of ferricyanide.

10. The assay system of claim 6 wherein the non-chromogenic competing reactant is a weak oxidizing agent selected from the group consisting of trichloromelanine, hydrogen peroxide, and an organic peroxide.

11. The assay system of claim 9 wherein the salt is a sodium or potassium salt.

12. The assay system of claim 10 wherein the organic peroxide is selected from the group consisting of a lower alkyl peroxide and benzoyl peroxide.

13. The assay system of claim 1 wherein the catalyst is diaphorase and non-chromogenic competing reactant is not a substrate for the diaphorase.

14. The assay system of claim 1 wherein the catalyst is an organic polycyclic compound.

15. The assay system of claim 14 wherein the catalyst is an organic polycyclic compound selected from the group consisting of medola blue, phenazonium methosulfate, N-methyl-phenazonium methosulfate, methylene blue and anthraquinones substituted with a member selected from the group consisting of methyl-, chloro-, bromo-, amino-, hydroxy-, nitro-, methoxy and sulfonic acid.

16. The assay system of claim 1 which further comprises a metal salt which enhances the catalytic activity of the catalyst.

17. The assay system of claim 16 wherein the catalyst is an organic ligand complex of the metal salt.

18. The assay system of claim 7 wherein the catalyst is ferrocene.

19. The assay system of claim 1 wherein the chromogen is a tetrazolium salt.

20. The assay system of claim 1 wherein the concentration of an analyte which reacts to form or consume NAD(P)H is measured.

21. The assay system of claim 20 wherein the analyte is selected form the group consisting of glucose, alcohol, lactic acid, glycerol, ketones and beta-hydroxybutyrate.

22. The assay system of claim 21 wherein the analyte is generated in situ, and wherein the assay system further comprises an NAD(P)-dependent dehydrogenase capable of oxidizing the analyte.

23. The assay system of claim 1 wherein said assay system comprises a series of defined areas, and wherein each area contains the non-chromogenic competing reactant in different preselected concentrations, wherein each different preselected concentration is capable of preventing a visible color change due to accumulation of reduced chromogen until a different predetermined threshold amount of NAD(P)H is exceeded, and wherein a visible color change is indicative of an amount of NAD(P)H above the predetermined threshold and the absence of a visible color change is indicative of an amount of NAD(P)H below the predetermined threshold.

24. The assay system of claim 23 wherein the concentration of an analyte which reacts to form or consume NAD(P)H is measured.

25. The assay system of claim 23, wherein the assay system further comprises an NAD(P)-dependent dehydrogenase capable of oxidizing the analyte.

26. The assay system of claim 23 wherein the analyte is selected from the group consisting of glucose, alcohol, lactic acid, glycerol, ketones and beta-hydroxybutyrate.

27. The assay system of claim 26 wherein the analyte is generated in situ.

28. The assay system of claim 23 wherein the catalyst is an organic polycyclic compound, the chromogen is a tetrazolium salt and the non-chromogenic competing reactant is a weak oxidizing agent which accepts electrons more readily than NAD(P).

29. The assay system of claim 28 wherein the non-chromogenic competing reagent is selected from the group consisting of triethyldiamine salt of Fe(III), Fe(III) EDTA complex, Fe(III) sorbitol complex, hexamino cobalt (III) chloride, potassium hexacyanocobaltate (III) and sodium hexanitrocobaltate (III).

30. The assay system of claim 28 wherein the non-chromogenic competing reactant is selected from the group consisting of sodium potassium periodate, paranitrobenzyl disulfide and 2,2'-diathiobis (4-tert-butyl-1-isopropyl imidazole).

31. The assay system of claim 28 wherein the non-chromogenic competing reactant is a water-soluble alkali metal salt of ferricyanide.

32. The assay system of claim 31 wherein the salt is a sodium or potassium salt.

33. The assay system of claim 28 wherein the non-chromogenic competing reactant is a weak oxidizing agent selected from the group consisting of trichloromelanine, hydrogen peroxide and organic peroxides.

34. The assay system of claim 33 wherein the organic peroxide is selected from the group consisting of a lower alkyl peroxide and benzoyl peroxide.

35. The assay system of claim 1 wherein the non-chromogenic competing reactant is capable of reoxidizing dye formed upon the reduction of the chromogen.

36. The assay system of claim 1 wherein the sample is urine, the analyte is uric acid, and the concentration of uric acid is determined.

37. The assay system of claim 1 wherein the sample is saliva, the analyte is alcohol, and the concentration of alcohol is determined.

38. The assay system of claim 1 wherein the sample is blood, the analyte is cholesterol, and the concentration of cholesterol is determined.

39. The assay system of claim 1, wherein the concentration of an analyte which reacts to form NAD(P)H is determined and the assay system further comprises an NAD(P)-dependent dehydrogenase capable of oxidizing the analyte.

40. A diagnostic colorimetric device for determination of the concentration of NAD(P)H, NAD(P), or an analyte which reacts to form or consume NAD(P)H, wherein the device comprises:
a physical support means,
a chromogen which is capable of accepting electrons from NAD(P)H and which produces a color change upon reduction by NAD(P)H,
a non-chromogenic competing reactant which is capable of accepting electrons from NAD(P)H, in an amount sufficient to prevent a visible color change due to accumulation of reduced chromogen until a predetermined threshold amount of NAD(P)H is exceeded, an electron-carrier catalyst capable of transferring electrons from NAD(P)H to the chromogen, a coenzyme selected from the group consisting of NAD(P) and NAD(P)H, wherein a visible color change is indicative of an amount of NAD(P)H above the predetermined threshold and the absence of a visible color change is indicative of an amount of NAD(P)H below the predetermined threshold.

41. The device of claim 40 wherein the coenzyme is NAD(P).

42. The device of claim 40 wherein the physical support means is a water-absorbing material.

43. The device of claim 42 wherein the water-absorbing material is selected from the group consisting of chromogenic pater, gelatin and a synthetic resin.

44. The device of claim 40 wherein the physical support means is a synthetic resin selected from the group consisting of polyethylene, polypropylene, polyalkyleneacetate and polycarbonate.

45. The device of claim 42 wherein the water-absorbing material is a multilayer dry gel inside a controlled volume capillary.

46. The device of claim 45 wherein the gel is selected from the group consisting of gelatin, agarose, agar, polyvinyl alcohol, polyvinyl pyrolidone, alginate, carrageenan, dextran, xanthan gum and mixtures thereof.

47. The device of claim 42 wherein the physical support means are in a form selected from the group consisting of sheets, rods, webs, filters and strips.

48. The device of claim 42 wherein the water absorbing material is a metal oxide.

49. The device of claim 48 wherein the water absorbing metal oxide is a controlled pore alumina catalytic ring.

50. The device of claim 42 wherein the water-absorbing material is a hybrid ceramic/polymer.

51. The device of claim 50 wherein the hybrid ceramic/polymer material is a polyvinyl chloride sheet that contains embedded silica particles.

52. The device of claim 42 wherein the physical support means is selected from the group consisting of glass, cellulose, wood, metal and textiles.

53. The device of claim 42 wherein the physical support means is a controlled-pore polycarbonate membrane.

54. The device of claim 52 wherein the concentration of non-chromogenic competing reactant to NAD(P)H at the threshold is either 1 to 1 or 2 to 1.

55. The device of claim 40 wherein the non-chromogenic competing reactant is a weak oxidizing agent which accepts electrons more readily than NAD(P).

56. The device of claim 55 wherein the catalyst is an organic polycyclic compound, and the chromogen is a tetrazolium salt.

57. The device of claim 40 which further comprises a metal salt capable of enhancing the catalytic activity of the catalyst.

58. The device of claim 40 wherein the concentration of an analyte which reacts to form or consume NAD(P)H is measured.

59. The device of claim 58 which further comprises an NAD(P)-dependent dehydrogenase capable of oxidizing the analyte.

60. The device of claim 59 wherein the analyte is selected from the group consisting of alcohol, lactic acid, glucose, glycerol, ketones and beta-hydroxybutyrate.

61. The device of claim 60 wherein the analyte is generated in situ.

62. The device of claim 58 wherein the analyte is generated in situ from triglyceride.

63. The device of claim 59 wherein the analyte is generated in situ.

64. The device of claim 40 wherein the non-chromogenic competing reactant is capable of reoxidizing dye formed upon the reduction of the chromogen.

65. A diagnostic colorimetric device for determination of the concentration of NAD(P)H, NAD(P), or an analyte which reacts to form or consume NAD(P)H, wherein the device comprises:

a physical support means, a chromogen which is capable of accepting electrons from NAD(P)H and which produces a color change upon reduction by NAD(P)H, a non-chromogenic competing reactant which is capable of accepting electrons from NAD(P)H, in an amount sufficient to prevent a visible color change due to accumulation of reduced chromogen until a predetermined threshold amount of NAD(P)H is exceeded, an electron-carrier catalyst capable of transferring electrons from NAD(P)H to the chromogen, wherein the physical support means has a series of defined areas, each area containing a different preselected concentration of the non-chromogenic competing reactant and wherein each pre-selected concentration of non-chromogenic competing reactant is capable of preventing a visible color change due to accumulation of reduced chromogen until a predetermined threshold amount of NAD(P)H is exceeded.

66. The device of claim 65 wherein the non-chromogenic competing reactant is a weak oxidizing agent which accepts electrons more readily than NAD(P).

67. The device of claim 65 wherein the concentration of an analyte which reacts to form or consume NAD(P)H is measured.

68. The device of claim 67 which further comprises an NAD(P)-dependent dehydrogenase capable of oxidizing the analyte.

69. The device of claim 68 wherein the analyte is selected from the group consisting of glucose, alcohol, lactic acid, glycerol, ketones and beta-hydroxybutyrate.

70. The device of claim 68 wherein the analyte is generated in situ.

71. The device of claim 65 wherein the non-chromogenic competing reactant is capable of reoxidizing dye formed upon the reduction of the chromogen.

72. A diagnostic colorimetric device for determination of the concentration of NAD(P)H, NAD(P), or an analyte which reacts to form or consume NAD(P)H, wherein the device comprises:

a physical support means, a chromogen which is capable of accepting electrons from NAD(P)H and which produces a color change upon reduction by NAD(P)H, a non-chromogenic competing reactant which is capable of accepting electrons from NAD(P)H, in an amount sufficient to prevent a visible color change due to accumulation of reduced chromogen until a predetermined threshold amount of NAD(P)H is exceeded, an electron-carrier catalyst capable of transferring electrons from NAD(P)H to the chromogen, NAD(P), and an NAD(P)-dependent dehydrogenase capable of oxidizing the analyte to produce NAD(P)H in an amount proportional to the analyte, wherein the physical support means has a series of defined areas, each area containing a different pre-selected concentration of the non-chromogenic competing reactant and wherein each pre-selected concentration of non-chromogenic competing reactant is capable of preventing a visible color change due to accumulation of reduced chromogen until a predetermined threshold amount of NAD(P)H is exceeded.

73. The device of claim 72, wherein the non-chromogenic competing reactant is capable of reoxidizing dye formed upon the reduction of the chromogen.

74. A digital colorimetric method for determining the amount of an organic analyte in a sample, wherein the method comprises:
  (a) contacting the sample with an assay system comprising an NAD(P)-dependent dehydrogenase capable of oxidizing the analyte to produce NAD(P)H in an amount proportional to the analyte, NAD(P), a chromogen capable of producing a color change upon reduction by NAD(P)H in the presence of an electron-carrier catalyst, an electron-carrier catalyst, and a non-chromogenic competing reactant capable of accepting electrons from NAD(P)H, wherein the non-chromogenic competing reactant is present in an amount sufficient to prevent a visible color change due to accumulation of reduced chromogen until a predetermined threshold amount of NAD(P) is exceeded, and
  (b) determining the amount of NAD(P)H as an indirect determination of the analyte, wherein a visible color change is indicative of an amount of NAD(P)H above the predetermined threshold an the absence of a visible color change is indicative of an amount of NAD(P)H below the predetermined threshold.

75. The method of claim 74 wherein the analyte is selected from the group consisting of glucose, alcohol, lactic acid, glycerol, ketones and beta-hydroxybutyrate.

76. The method of claim 74 wherein the non-chromogenic competing reactant is capable of reoxidizing dye formed upon the reduction of the chromogen.

77. The method of claim 74 wherein the analyte is generated in situ.

78. The method of claim 74 wherein the sample is not diluted prior to adding the sample to the assay system.

79. The method of claim 74 wherein the sample is urine and the analyte is uric acid.

80. The method of claim 74 wherein the sample is saliva and the analyte is alcohol.

81. The method of claim 74 wherein the sample is blood and the analyte is cholesterol.

82. The device of claim 40 wherein the catalyst is diaphorase and the non-chromogenic competing reactant is not a substrate for the diaphorase.

83. The device of claim 65 wherein the catalyst is diaphorase and the non-chromogenic competing reactant is not a substrate for the diaphorase.

84. The device of claim 72 wherein the catalyst is diaphorase and the non-chromogenic competing reactant is not a substrate for the diaphorase.

85. The method of claim 75 wherein the catalyst is diaphorase and the non-chromogenic competing reactant is not a substrate for the diaphorase.

* * * * *

UNITED STATES PATENT AND TRADEMARK OFFICE
CERTIFICATE OF CORRECTION

PATENT NO. : 5,036,000

DATED : July 30, 1991

INVENTOR(S) : John L. Palmer and Marsha W. Timmerman

It is certified that error appears in the above-identified patent and that said Letters Patent is hereby corrected as shown below:

Col. 16, Claim 7, line 67, change "hexcacyanocobaltate" to

--hexacyanocobaltate--.

Col. 17, Claim 13, line 20, after "and" insert --the--.

Col. 19, Claim 43, line 16, change "pater" to --paper--.

Col. 22, Claim 74, line 2, change "an to --and--.

Signed and Sealed this

Twenty-second Day of December, 1992

*Attest:*

DOUGLAS B. COMER

*Attesting Officer*    Acting Commissioner of Patents and Trademarks